(12) United States Patent
Montagu

(10) Patent No.: US 7,158,224 B2
(45) Date of Patent: Jan. 2, 2007

(54) OPTICALLY ACTIVE SUBSTRATES

(75) Inventor: Jean I. Montagu, Brookline, MA (US)

(73) Assignee: Affymetrix, Inc., Santa Clara, CA (US)

( * ) Notice: Subject to any disclaimer, the term of this patent is extended or adjusted under 35 U.S.C. 154(b) by 215 days.

(21) Appl. No.: 10/311,820

(22) PCT Filed: Jun. 25, 2001

(86) PCT No.: PCT/US01/20177

§ 371 (c)(1),
(2), (4) Date: Dec. 19, 2002

(87) PCT Pub. No.: WO02/01194

PCT Pub. Date: Jan. 3, 2002

(65) Prior Publication Data

US 2004/0125370 A1 Jul. 1, 2004

Related U.S. Application Data

(60) Provisional application No. 60/213,987, filed on Jun. 25, 2000.

(51) Int. Cl.
*G01N 21/01* (2006.01)

(52) U.S. Cl. ................................... 356/244

(58) Field of Classification Search ............. 356/344, 356/39, 432–448, 300–311, 244–235; 250/339.07–339.11; 600/322–324
See application file for complete search history.

(56) References Cited

U.S. PATENT DOCUMENTS 4,400,056 A    8/1983  Cielo ..................... 350/96.19
4,604,520 A    8/1986  Pohl ...................... 250/216
4,649,280 A    3/1987  Holland et al. .......... 250/483.1
4,681,451 A    7/1987  Guerra et al. ............ 356/373
4,815,843 A    3/1989  Tiefenthaler et al. ..... 356/128
4,917,462 A    4/1990  Lewis et al. ............. 350/319
5,004,307 A    4/1991  Kino et al. .............. 350/1.2
5,018,865 A    5/1991  Ferrell et al. ........... 356/376
5,028,802 A    7/1991  Webb et al. ............. 250/571
5,081,012 A    1/1992  Flanagan et al. ......... 435/7.9
5,082,629 A    1/1992  Burgess, Jr. et al. ..... 422/82.11
5,120,131 A    6/1992  Lukosz ................... 356/351
5,125,750 A    6/1992  Corle et al. ............. 359/819
5,166,515 A    11/1992 Attridge ................. 250/227.25
5,272,330 A    12/1993 Betzig et al. ............ 250/216
5,304,795 A    4/1994  Fujihira et al. .......... 250/234
5,341,215 A    8/1994  Scher .................... 356/445

(Continued)

FOREIGN PATENT DOCUMENTS

WO     WO 92/15862       9/1992

(Continued)

OTHER PUBLICATIONS

Fluorometer and tapered fiber optic probes for sensing in the evanescent wave Golden, et al; Optical Engineering/Jul. 1992/vol. 31 No. 7 pp. 1458-1462.

*Primary Examiner*—Tu T. Nguyen
(74) *Attorney, Agent, or Firm*—Ivan Zitkovsky

(57) ABSTRACT

A device for optical examination of biological materials using radiation of a selected wavelength includes a substrate having a first surface and a second surface opposite to the first surface. The first surface includes a dense array of micro-optical elements arranged to provide increased intensity radiation or evanescent radiation. The first surface is in close proximity to the biological material being examined.

46 Claims, 6 Drawing Sheets

U.S. PATENT DOCUMENTS

| | | | | |
|---|---|---|---|---|
| 5,351,127 | A | 9/1994 | King et al. | 356/445 |
| 5,351,318 | A | 9/1994 | Howell et al. | 385/3 |
| 5,352,582 | A | 10/1994 | Lichtenwalter et al. | 435/6 |
| 5,369,717 | A | 11/1994 | Attridge | 385/12 |
| 5,410,151 | A | 4/1995 | Buckland | 250/227.26 |
| 5,424,841 | A | 6/1995 | Van Gelder et al. | 356/417 |
| 5,437,840 | A | 8/1995 | King et al. | 422/82.08 |
| 5,442,169 | A | 8/1995 | Kunz | 250/227.21 |
| 5,452,382 | A | 9/1995 | Shionoya et al. | 385/11 |
| 5,478,755 | A | 12/1995 | Attridge et al. | 436/518 |
| 5,485,536 | A | 1/1996 | Islam | 385/31 |
| 5,497,359 | A | 3/1996 | Mamin et al. | 369/44.15 |
| 5,548,113 | A | 8/1996 | Goldberg et al. | 250/234 |
| 5,577,137 | A | 11/1996 | Groger et al. | 385/12 |
| 5,578,818 | A | 11/1996 | Kain et al. | 250/234 |
| 5,585,639 | A | 12/1996 | Dorsel et al. | 250/458.1 |
| 5,631,170 | A | 5/1997 | Attridge | 436/518 |
| 5,633,724 | A | 5/1997 | King et al. | 356/445 |
| 5,664,036 | A | 9/1997 | Islam | 385/31 |
| 5,675,145 | A | 10/1997 | Toda et al. | 250/234 |
| 5,689,480 | A | 11/1997 | Kino | 369/14 |
| 5,712,705 | A | 1/1998 | Fattinger et al. | 356/354 |
| 5,736,410 | A | 4/1998 | Zarling et al. | 436/172 |
| 5,738,825 | A | 4/1998 | Rudigier et al. | 422/82.11 |
| 5,754,514 | A | 5/1998 | Guerra | 369/116 |
| 5,763,870 | A | 6/1998 | Sadler et al. | 250/201.2 |
| 5,764,840 | A | 6/1998 | Wach | 385/123 |
| 5,796,487 | A | 8/1998 | Guerra | 356/376 |
| 5,796,909 | A | 8/1998 | Islam | 385/147 |
| 5,800,992 | A | 9/1998 | Fodor et al. | 435/6 |
| 5,808,790 | A | 9/1998 | Otaki | 359/387 |
| 5,812,272 | A | 9/1998 | King et al. | 356/445 |
| 5,812,723 | A | 9/1998 | Ohtsu et al. | 385/128 |
| 5,821,410 | A | 10/1998 | Xiang et al. | 73/105 |
| 5,822,472 | A | 10/1998 | Danielzik et al. | 385/12 |
| 5,827,748 | A | 10/1998 | Golden | 436/527 |
| 5,837,475 | A | 11/1998 | Dorsel et al. | 435/7.1 |
| 5,859,814 | A | 1/1999 | Kino et al. | 369/13 |
| 5,871,628 | A * | 2/1999 | Dabiri et al. | 204/461 |
| 5,883,872 | A | 3/1999 | Kino | 369/112 |
| 5,892,857 | A | 4/1999 | McCallion | 385/1 |
| 5,900,949 | A | 5/1999 | Sampas | 358/482 |
| 5,907,425 | A | 5/1999 | Dickensheets et al. | 359/224 |
| 5,910,940 | A | 6/1999 | Guerra | 369/275.1 |
| 5,928,525 | A | 7/1999 | Ohtsu et al. | 216/24 |
| 5,939,709 | A | 8/1999 | Ghislain et al. | 250/216 |
| 5,945,679 | A | 8/1999 | Dorsel et al. | 250/458.1 |
| 5,953,477 | A | 9/1999 | Wach et al. | 385/115 |
| 5,959,292 | A | 9/1999 | Duveneck et al. | 250/227.11 |
| 5,969,345 | A | 10/1999 | Williams et al. | 250/234 |
| 5,971,193 | A | 10/1999 | Sadler et al. | 359/599 |
| 5,980,831 | A | 11/1999 | Braiman et al. | 422/82.11 |
| 5,982,716 | A | 11/1999 | Kino et al. | 369/14 |
| 6,002,704 | A | 12/1999 | Freitag et al. | 372/94 |
| 6,006,119 | A * | 12/1999 | Soller et al. | 600/322 |
| 6,016,376 | A | 1/2000 | Ghaemi et al. | 385/116 |
| 6,026,205 | A | 2/2000 | McCallion et al. | 385/30 |
| 6,064,785 | A | 5/2000 | Sugiura | 385/30 |
| 6,078,705 | A | 6/2000 | Neuschafer et al. | 385/12 |
| 6,140,044 | A | 10/2000 | Besemer et al. | 435/6 |
| 6,177,990 | B1 | 1/2001 | Kain et al. | 356/246 |
| 6,198,869 | B1 | 3/2001 | Kraus et al. | 385/129 |
| 6,201,639 | B1 | 3/2001 | Overbeck | 359/368 |
| 6,294,327 | B1 | 9/2001 | Walton | 435/6 |
| 6,393,035 | B1 | 5/2002 | Weingarten et al. | 372/18 |
| 6,395,558 | B1 | 5/2002 | Duveneck et al. | 436/172 |
| 6,437,345 | B1 | 8/2002 | Bruno-Raimondi et al. | 250/458.1 |
| 2002/0132261 | A1 | 9/2002 | Dorsel et al. | 435/6 |

FOREIGN PATENT DOCUMENTS

| | | |
|---|---|---|
| WO | WO 95/33197 | 12/1995 |
| WO | WO 96/18205 | 6/1996 |
| WO | WO 96/36062 | 11/1996 |
| WO | WO 97/28439 | 8/1997 |
| WO | WO 98/22799 | 5/1998 |
| WO | WO 98/52481 * | 11/1998 |
| WO | WO 99/13320 | 3/1999 |
| WO | WO 99/47705 | 9/1999 |
| WO | WO 99/63326 | 12/1999 |
| WO | WO 00/20848 | 4/2000 |
| WO | WO 00/62105 | 10/2000 |
| WO | WO 01/18524 | 3/2001 |
| WO | WO 01/79821 | 10/2001 |

* cited by examiner

OPTICALLY ACTIVE SUBSTRATES

BACKGROUND OF THE INVENTION

This application claims priority from U.S. Provisional Application Ser. No. 60/213,987, filed on Jun. 25, 2000, entitled Optically Active Substrates, which is incorporated by reference.

The present invention relates to detecting and analyzing biological materials by optical scanning, and particularly relates to optical scanning or imaging of biological materials located on optically active substrates.

Microarray technology enables studying complex biochemical reactions and systems at once instead of studying them individually. The technology provides a massively parallel form of analysis that increases data collection per unit time, decreases the overall time required for analysis, uses smaller sample volumes and reagent volumes and sometimes reduces disposable consumption. Although the initial cost may be high, overall the technology represents considerable savings in the time and costs of associated labor. Microarray technology became a fundamental tool for genomic research. The technology can also be utilized for routine analysis used in clinical diagnostics or for industrial analytical purposes.

In general, microarrays can be created by optical (or other radiation) directed synthesis, or by microfluidic delivery of nucleic acids onto different substrates. The first technique uses photolithography or other submicron technologies to define positions at which single specific nucleotides are added to growing single-stranded nucleic acid chains. Series of precisely defined nucleotide additions and light directed chemical linking steps are used to synthesize high-density arrays of defined oligonucleotides on a solid substrate. A microarray of probe sequences may be fabricated by using techniques described in U.S. Pat. No. 5,143,854 or PCT Application published as WO 92/10092, or U.S. Pat. Nos. 5,384,261; 5,405,783; 5,412,087; 5,424,186; 5,445,934; 5,744,308 all of which are incorporated by reference. Alternatively, microarrays can be fabricated by other techniques as described in PCT Application PCT/US99/18438 published as WO 00/09757, which is incorporated by reference.

According to a second technique, microarrays are created by microfluidic delivery, as described in PCT Application PCT/US99/00730, published as WO 99/36760, which is incorporated by reference. These microarrays can contain a wide range of biological materials including, plant, animal, human, fungal and bacteria cells; viruses, peptides, antibodies, receptors, and other proteins; cDNA clones, DNA probes, oligonucleotides, polymerase chain reactions (PCR) products, and chemicals. These biological materials are delivered in form of an array of spots to various microarray substrates including chemically treated glass microscope slides, coverslips, plastics, membranes, or gels. The number of deposited spots is in the range of 100 to 50,000 per microarray, and the diameter of an individual spot is in the range of 50 µm to 1000 µm, and preferably 100 µm to 250 µm. The volume of each deposited spot is in the range of 10 pL to 10 nL, and preferably 50 pL to 500 pL.

There are several types of microarray scanning and imaging systems for viewing the entire microarray. Myles et al. described different optical scanning and imaging systems in *Microarray Biochip Technology*, pp. 53–64, edited by M. Schena, published by BioTechniques Books, Natick, Mass. These scanning systems utilize XYZ stage scanning with a stationary microscope objective, pre-objective scanning, or flying objective scanning with a translation stage. Some fluorescence microscopes use a CCD array imager as a detector. Numerous examples are described in the Handbook of Biological Confocal Microscopy edited by James Pawley, Plenum Press, 1989 and 1995, or by Sampas in U.S. Pat. No. 5,900,949.

Many of the above-mentioned instruments are epifluorescent pseudo-confocal laser scanning microscopes. They are pseudo-confocal systems because they have two optical paths. The first path is the excitation path (also called laser path) that defines the pixel size, typically between 3 and 10 µm. This path has a relatively low numerical aperture, around 0.1, and consequently a greater depth of field. The second path is the emission path (also called detection path), designed to maximize energy collection and therefore has the highest possible numerical aperture; however, this provides a small depth of field. A true confocal microscope uses the same numerical aperture for both lenses and a relatively small depth of field, which is used to create "optical sections" of three-dimensional structures. The confocal microscopy is used to reject out of focus background signal.

The depth of field expresses the axial tolerance in locating the sample in order to obtain a valid measurement of a picture element (i.e., a pixel) needed to construct an image. The depth of field is also determined by the necessity to accommodate some irregularities of the large size of the slide or sample inspected. The depth of field (DOF) of a microscope is a function of the energy collection capability of the objective lens as defined by its numerical aperture (NA) and the light wavelength ($\lambda$), wherein $DOF \approx \lambda/(NA)^2$. The desired resolution of an image depends on the spot size (d) of the optical system expressed as a function of the numerical aperture (NA) of a perfect objective and the light wavelength ($\lambda$), wherein $d \approx \lambda/NA$.

The energy an optical system gathers in order to have a meaningful signal from the detector is expressed at a first approximation by the second power of the numerical aperture of the objective lens. The numerical aperture is a function of the lens geometry and the index of refraction (n) of the medium, i.e., $NA = n \sin \theta$, where $\theta$ is the angle formed by the radius of the lens and its focal distance, and $n=1$ in air. For example, for an objective with $NA=0.7$ used with visible light, DOF is about 2 micron; however, an objective with $NA=0.2$ collects less than about $1/10$ of light as the objective having $NA=0.7$, but it has $DOF=37$ microns.

Practical considerations for microarray scanning require a large depth of field to accommodate a lens, a scanning stage, substrate flatness and tolerances, and other imperfections. Consequently, there has to be a compromise between the amount of light collected (i.e., the size of NA) and the required depth of field. That is, microarray scanning and imaging instruments require several performance trade-offs.

Fluorescence microscopy is a relatively inefficient process, wherein the light source-to-detector efficiency is estimated in parts per trillions. There is usually a very low efficiency of the fluorescence conversion. Furthermore, among other limitations, the scanning systems cannot increase the intensity of the illumination by the laser source, because the fluorescent sample would be destroyed; this is known as photo-bleaching. Also, before photo-bleaching takes place, most fluorophores behave in a non-linear and possibly unpredictable manner. Additionally, numerous non-optical constrains come into play such as acceptable scan duration, detector performance, and electronic and image manipulation processes.

Therefore, there is a need for optical scanning or imaging systems with high source-to-detector efficiency and for sample substrates and packaging that efficiently utilize light for optical scanning and imaging.

SUMMARY OF THE INVENTION

The present invention relates to a system, product, and method for detecting and analyzing biological materials by optical scanning. The present invention utilizes optically active substrates that are used with various probes for detecting or analyzing biological material such as polymers. The optically active substrates may also provide an optically cooperating support for arrays of polymer sequences, such as oligonucleotide arrays.

According to one aspect, a device for optical examination of biological material using radiation of a selected wavelength, includes a substrate having a first surface and a second surface opposite to the first surface. The first surface comprises a dense array of micro-optical elements being arranged to form "increased intensity" radiation near the elements. The first surface is in close proximity to biological material being examined.

According to another aspect, a wide field of view, scanning microscope for examination of biological material on a first surface of an optically active substrate comprises a scanning assembly for an objective lens. The scanning assembly includes a support structure associated with a driver and constructed to travel in a periodic motion over the substrate in a predetermined linear or arcuate scan path. The objective lens delivers light for essentially on-axis scanning throughout a scan range of the assembly. The driver for the support structure is adapted to displace the support structure. The objective lens also collects light from the optically active substrate.

Preferred embodiments of these aspects include one or more of the following features. The second surface of the device (i.e., the optically active substrate) is oriented for receiving the radiation emitted from a light source of a scanning microscope. The second surface of the device is also oriented for providing radiation to a detector of a scanning microscope after interaction of the increased intensity radiation with the biological material.

The micro-optical elements are, for example, semi-spherical, aspherical, semi-conical, semi-hyperbolic, semi-parabolic or semi-triangular micro-lenses. Alternatively, the micro-lenses are formed by micro-cavities having parallel or semi-parallel groves in the form of half cylinders, quarter cylinders, cones, spheres, triangles, hyperbolas, ovaloids, or other geometrical shapes. The micro-lenses are preferably formed by micro-cavities formed inside the substrate.

The micro-cavities may be formed inside the substrate by spherical indentations of approximately one radius or a fraction of radius in depth. There are numerous methods for forming the micro-cavities or micro-structures including molding, hot pressing or other. The micro-optical elements may include a grating or teeth-like structures.

The optically transparent substrate has a thickness between the first and second surface of about 1 mm. Each said micro-optical element has a dimension comparable to, or somewhat larger or smaller than the wavelength of the radiation. The surface of the micro-optical elements may include a layer of a high index medium transparent at the employed wavelengths. The high index medium is deposited by one of the following: sputtering, evaporation, or MOCVD.

The micro-optical elements may include high density micro-lenses having a high index of refraction. The high density micro-lenses with the high index of refraction are made by vacuum deposition onto the first surface.

The micro-optical elements may be micro-lenses or other elements formed inside or on the surface of the substrate, having a radius or other periodic dimension in the range of 0.1 μm to 10 μm, or for some structures less than 100 μm. Preferably, the dimensions are comparable to the wavelength.

The optically transparent substrate can be made of one of the following: polycarbonate disc, Mylar® based disc, PMMA disc, Plexiglas® disc or similar plastic disc with an index of refraction about 1.57. The optically transparent substrate can be also made of glass or quartz.

The first surface is arranged to support a probe array. The first surface is arranged to support fluorescently labeled biological material. Then, the substrate is made of a material transparent to fluorescent light emitted from fluorophores excited at their specific emission wavelength.

The high index coating is made of titanium dioxide with an index of refraction of about 2.4, gallium phosphate with an index of refraction of about 3.4 or other medium with suitable index and transmission coefficient at the wavelength. The high index coating is deposited by one of the following: sputtering, evaporation or MOCVD. The high index coating has a thickness in the range of about 10 nm to 1000 μm, and preferably in the range of about 0.1 μm to 10 μm, depending on the material. Preferably, the material has a thickness that causes low attenuation, i.e., acceptable optical losses, since these coatings have a relatively low coefficient of transmission.

The optically active substrates are used for scanning of deposited or attached biological material. The optically active substrates can support thin tissue sections (processed by washing away some of the tissue and other methods known in the art.) The optically active substrates can also support oligonucleotide spots or features arrayed on a uniform featureless flat hard or soft, porous, or non-porous material.

According to another preferred method, fluorescently labeled biological material is deposited on the optically active substrate. An optical system images the deposited biological material. An emitted excitation beam is delivered by an optical element (e.g., an objective) to illuminate a number of microlenses (or other optically active elements) that "focus" or "intensify" the excitation beam. This type of "intensified" radiation or evanescent radiation excites fluorophores that emit light at their specific emission wavelength. The emitted fluorescent radiation is detected by a detector.

The optical system may include several embodiments. For example, the emitted fluorescent radiation may be collected by the microlenses (or other types optically active elements located on the optically active substrate) and transmitted back through the substrate. In this arrangement, a detector receives the transmitted fluorescent radiation via an objective lens (or optical system) located in a reflection geometry. Alternatively, the emitted fluorescent radiation is collected by a lens (or an optical system) located in a transmission geometry. In this embodiment, the detector receives fluorescent (or non-fluorescent) radiation that doesn't travel back through the substrate. In the transmission geometry, the microlenses (or other types optically active elements) do not "intensify" the fluorescent radiation, but this radiation is not attenuated by the optically active substrate.

According to yet another aspect, a high-resolution epi fluorescent confocal microscope is made with extremely high numerical aperture (possibly as high as NA=3) with a sub-micron resolution and an extremely great depth of field.

According to yet another aspect, the optically active substrate is used with a chip cartridge (or chip package) described in U.S. Pat. No. 5,945,334.

DESCRIPTION OF THE PREFERRED EMBODIMENTS

Figure 1:
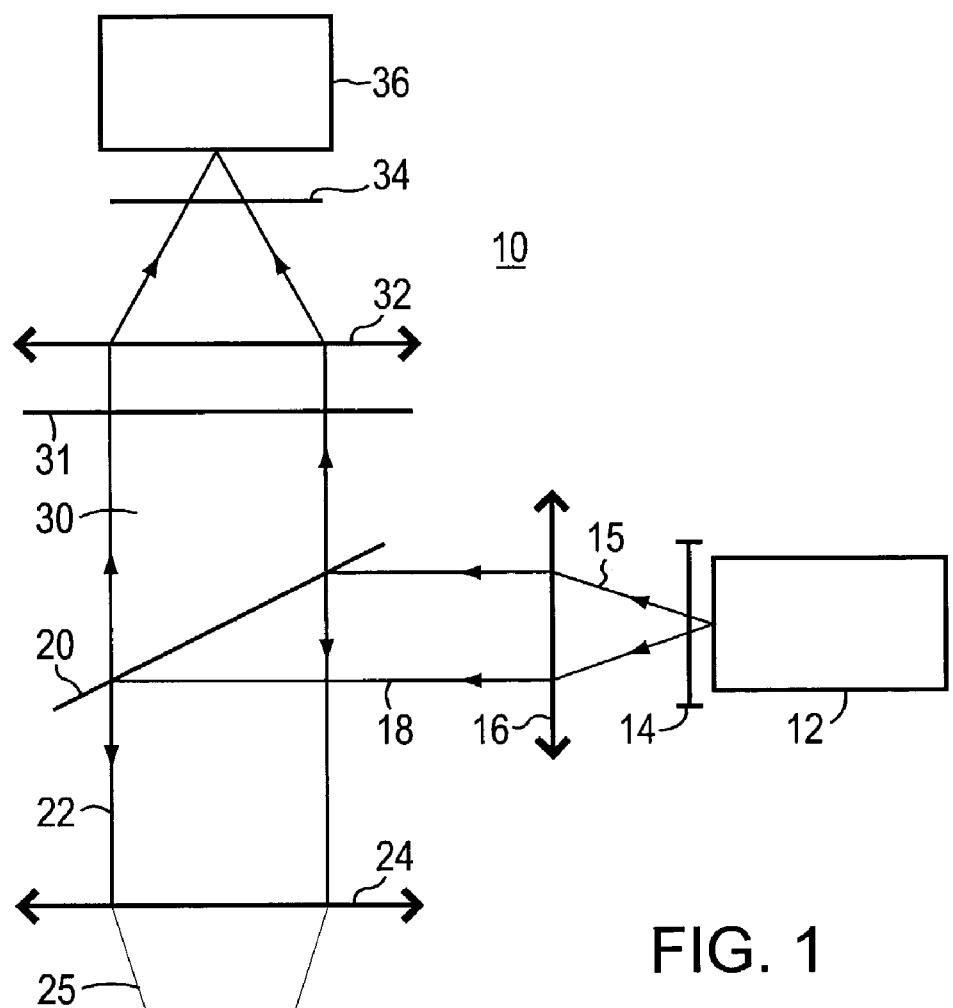
FIG. 1 is a schematic illustration of an optical scanning and imaging system.
Figure 3:
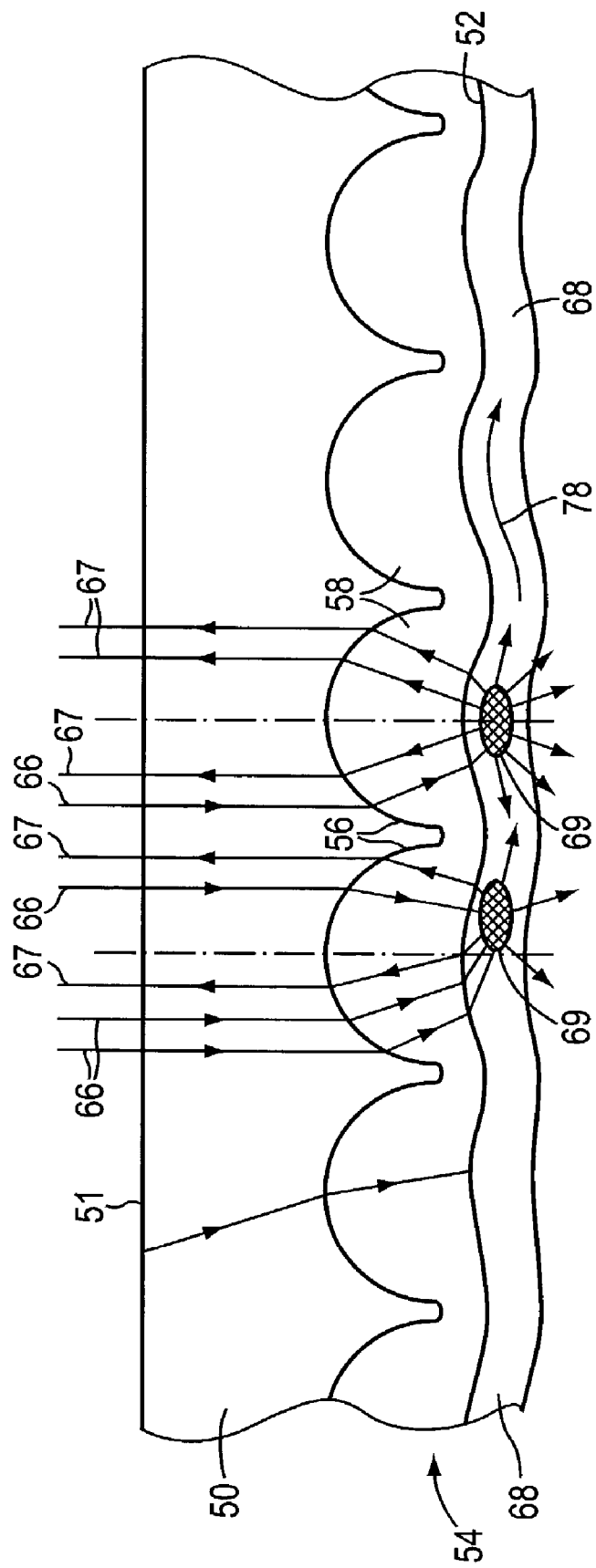
FIG. 3 shows an enlarged cross-sectional view of an optically active substrate.

FIG. 1 illustrates one embodiment of a confocal optical scanning and imaging system for examination of biological material located on, or near, an optically active substrate shown in FIG. 3. The optically active substrate forms an important part of the optical system designed for increasing the signal-to-noise ratio of the detected optical signal.

Referring to FIG. 1, optical system 10 includes a light source 12, an entrance aperture 14, a lens 16, a dichroic mirror 20, an objective lens 24, a two or three axis translation table 28, a lens 32, an exit pinhole 34, a band pass filter or a rejection filter 31 and a detector 36. In the following embodiment, optical system 10 is arranged for the detection of fluorescent light; however, optical system 10 may also be arranged for the detection of scattered or transmitted light at the irradiation wavelength.

Light source 12 emits an excitation light beam 15, and dichroic mirror 20 directs the excitation light toward objective lens 24. Objective lens 24 focuses light onto a pixel (A) located on or near an optically active substrate 26. Fluorescent light emitted from pixel A is collected by objective lens 24 and transmitted through dichroic mirror 20, over a light path 30, toward and trough band pass or rejection filter 31 and to light detector 36.

The arrangement of apertures (pinholes) 14 and 34 and lenses 16 and 32 provides to detector 36 fluorescent light from a selected depth (in the Z direction) of pixel A. At pixel A, light emitted from other depths in the Z direction is substantially blocked and doesn't pass through pinhole 34. This spatial filter improves the signal-to-noise ratio, which is known in the art.

Light source 12 is constructed to emit light of a wavelength capable of exciting fluorophores associated with the examined biological tissue located on the optically active substrate. As shown in FIG. 3, optically active substrate 50 is transparent and includes optically active surface 52 with a dense array of micro-optical elements 54. Micro-optical elements 54 are arranged to support biological material 68. Micro-optical elements 54 may be formed by microlens cavities 56 or other optical elements located on surface 52.

Figure 1A:
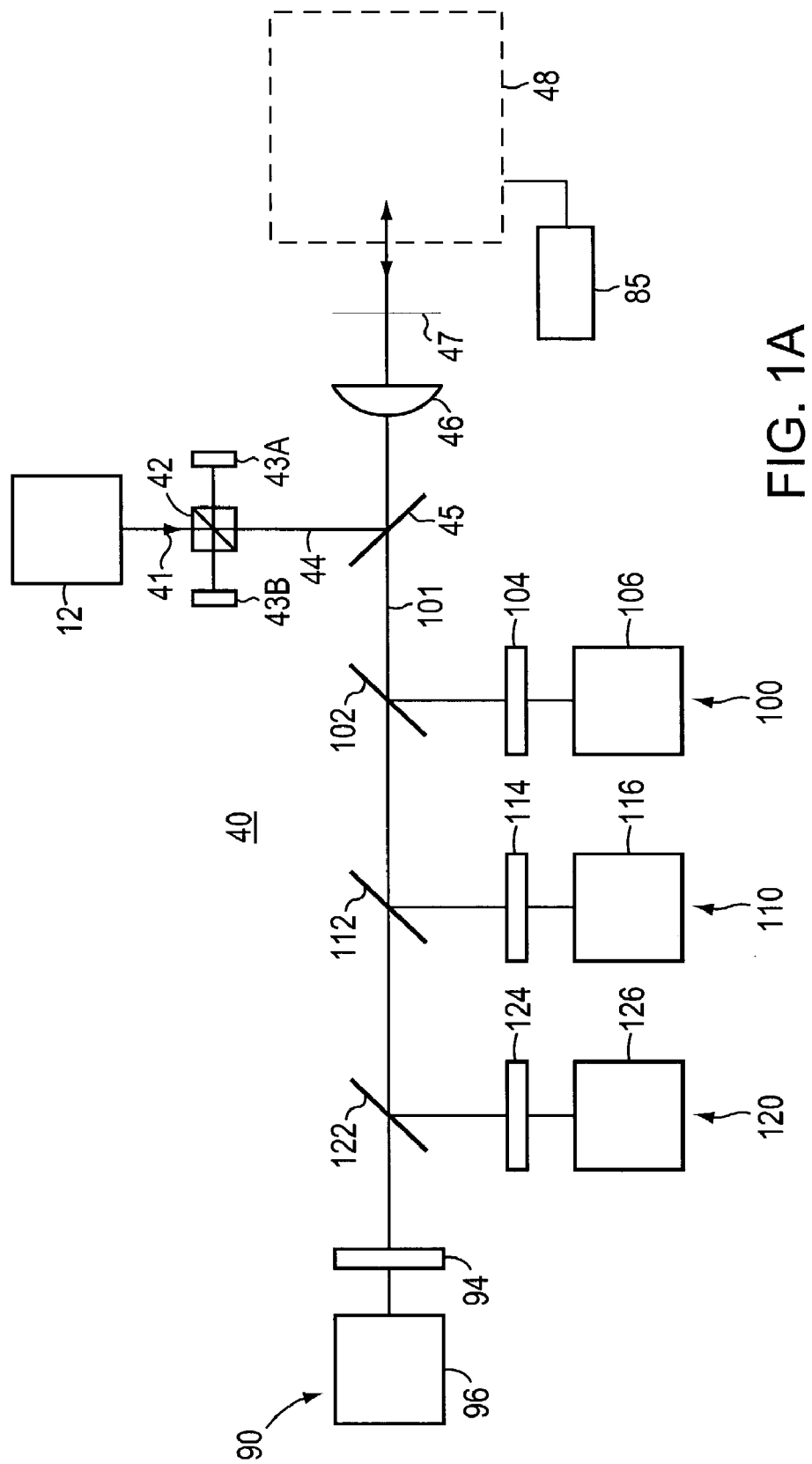
FIG. 1A is a schematic illustration of another optical scanning and imaging system.

Referring to FIGS. 1 and 1A, for example, light source 12 emits simultaneously or sequentially 473, 488 or 490 nm (or 532 nm, 638 nm or 745 nm) light directed to optically active substrate 26 by dichroic mirror 20. For example, the excitation light of 488 nm irradiates a pixel on the surface of substrate 26, and excites fluorophores that emit fluorescent light, for example, in the range 515 nm to 595 nm. The examined biological tissue can be labeled using various types of fluorophores (and their corresponding absorption maxima) are Fluorescein (488 nm), Dichloro-fluorescein (525 nm), Hexachloro-fluorescein (529 nm), Tetramethyl-rhodamine (550 nm), Rhodamine X (575 nm), Cy3™ (550 nm), Cy5™ (650 nm), Cy7™ (750 nm), and IRD40 (785 nm). Detector 36 uses a suitable band pass or rejection filters for detecting the fluorescent light emitted from pixel A. Preferably, objective lens 24 has a large numerical aperture (a numerical aperture of at least above 0.1). Optical system 10 can collect optical data over an array of pixels by displacing optically active substrate 26 (or optically active substrate 50) in the X and Y directions using a translation table 28.

In general, light source 12 may be a lamp with a filter or a laser (solid state or gas laser such as an argon laser, a helium-neon laser, a diode laser, a dye laser, a titanium sapphire laser, a frequency-doubled diode pumped Nd:YAG laser, or a krypton laser). Typically, the excitation source illuminates the sample with an excitation wavelength that is within the visible spectrum, but other wavelengths (i.e., ultraviolet or near infrared wavelengths) may be used depending on the type of markers or samples or detection methods. Light detector 36 may be a photomultiplier (PMT), a diode, a CCD array, or another photodetector.

FIG. 1A is a block diagram of an optical scanning system 40, which includes at least one light source, several optical detectors, a light path system for providing optical coupling, a fast scanning system, and a system controller. The light path system may include dichroic beamsplitters, spectral filters, pinholes and several channels for detecting wavelength specific radiation. The optical scanning system 40 also uses the novel optically active substrates described in detail in connection with FIG. 3.

The optically active surface has a dense array of micro-optical elements, each having a dimension comparable to (or larger than) the wavelength of the radiation emitted from the light source. The micro-optical elements are constructed and arranged to generate increased intensity radiation or excite an evanescent radiation in their close proximity. The optically active surface may be combined with other techniques for examination of biological material, which techniques are mentioned and incorporated by reference above. Typically, optical scanning system 10 or 40 is used to obtain images of oligonucleotide microarrays to which fluorescently labeled DNA or RNA is bound, images of polypeptides or other polymer arrays, electrophoresis gels, or other biological specimens. The optically active surface improves the efficiency of the detection process.

Referring to FIG. 1A, a controller 85 controls the entire operation of optical scanning system 40 including a beam scanner 48. Scanning system 40 specifically includes a laser 12 for providing radiation of a selected wavelength to a stationary light path system 12. In the stationary light path system, the emitted beam 41 is partially reflected and partially transmitted by a beamsplitter 42. The reflected portion of beam 41 impinges upon a photodetector 43B (optional), which is typically a photodiode used for laser power monitoring. The transmitted portion of beam 41, traveling over a light path 44, is reflected by a dichroic beamsplitter 45, transmitted through a lens 46 and an aperture (pinhole) 47, expanded to the desired diameter, and delivered to a beam scanner 48.

The beam scanning system, schematically shown as box 48, includes several optical elements arranged for scanning a sample that may be located on a linear translation stage. Beam scanning system 48 delivers sequentially a focused light beam to a series of pixels, and conveys reflected or fluorescent light from each pixel back to the light path system. Beam scanning system 48 has several high scan rate embodiments discussed in detail below.

Beam scanning system 48 also provides the "return" light path (shown in FIGS. 2 and 3) for light re-emitted from a sample, and focuses the re-emitted light onto confocal pinhole 47. Light transmitted through aperture 47 is collimated by lens 46. For example, light re-emitted from the sample having wavelengths less that 515 nm is reflected by beamsplitter 45 and partially reflected by beamsplitter 42 to arrive at photodetector 43A. (Alternatively, pinhole 47 may be located in a light path 101 to spatially filter only the fluorescent radiation). Light transmitted through beamsplitter 45 travels over light path 101 to the four optical channels 90, 100, 110 and 120 depending on its wavelength. The number of optical channels used in scanning system 40 is optional. For example, light of a wavelength between 515 μm and 545 nm, reflected by a dichroic beamsplitter 102, passes through a filter 104 onto a photodetector 106. Light reflected by a dichroic beamsplitter 112, having a wavelength between 545 nm and 570 nm passes through a filter 114 and onto a photodetector 116. Similarly, a photodetector 126 detects light having wavelengths between 570 nm and 595 nm, which passes through a filter 124. Light of wavelengths greater than 595 nm passes through a filter 94 onto a photodetector 96. Preferably, photodetectors 96, 106, 116, and 126 are photomultipliers (PMTs). Each optical channel 90, 100, 110 and 120 may include a confocal pinhole adjacent to a lens (not shown in FIG. 1). Confocal pinhole transmits florescence originating from the focal plane of system 10.

Figure 2:
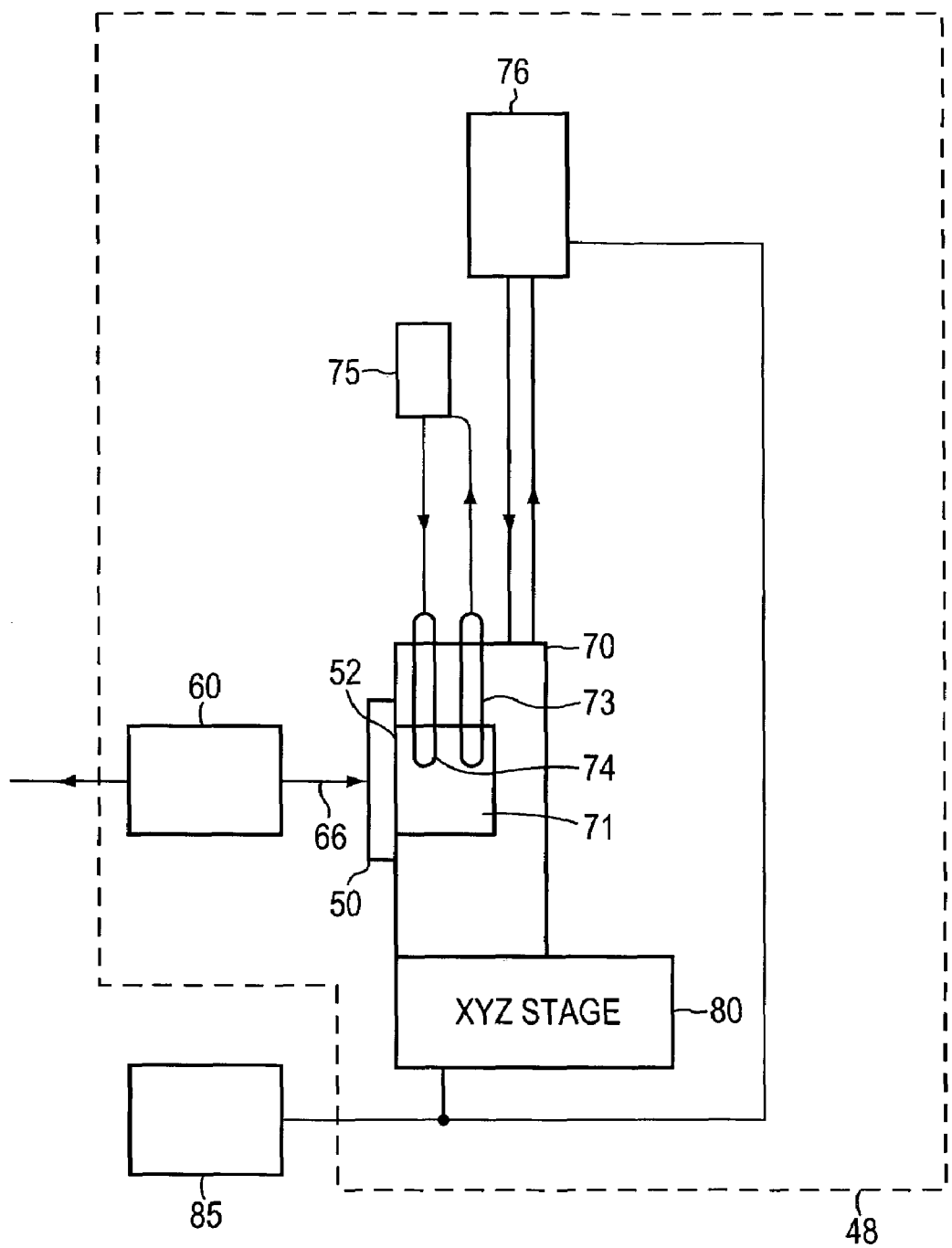
FIG. 2 shows diagrammatically a beam scanning system and a flow system used in the optical scanning and imaging system of FIG. 1A.

Referring to FIG. 2, beam scanning system 48 may include a flying objective design (an oscillatory movement design or a linear movement design), a scanning XY design, or preobjective scanning design. These designs are diagrammatically shown in FIG. 2 as a box 60 (e.g. comprising a flying objective, a scanning mirror etc.). Beam scanning system 48 provides an irradiation beam 49 directed toward an optically transparent substrate 50 mounted on a flow cell 70. For example, flow cell 70 is located on an XYZ stage 80 controlled by a controller 85 (which can also control the entire scanning system 40 and several elements of a hybridization system). Flow cell 70 includes a body having a cavity 71, which is about 50 μm to 1500 μm deep, having the bottom and sides of cavity 71 preferably light absorbing. Flow cell 70 includes an inlet port 73 and an outlet port 74.

Figure 2A:
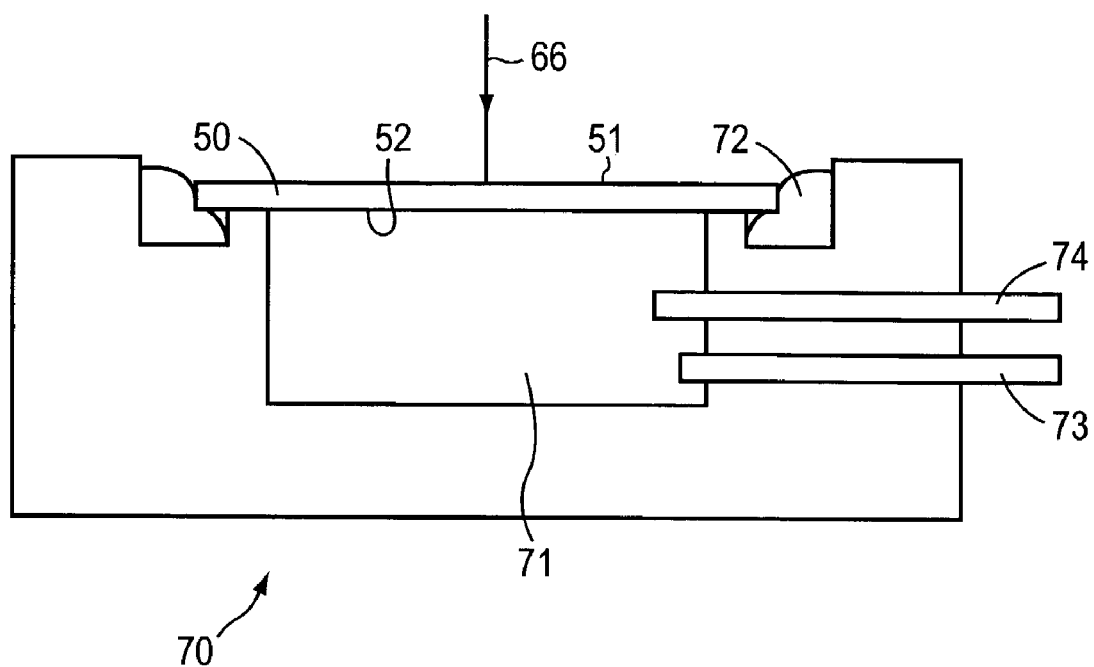
FIG. 2A is a detailed cross-sectional view of a flow cell used with an optically active substrate, as shown in FIG. 2.

FIG. 2A is a cross-sectional view of flow cell 70 with substrate 50 mounted on flow cell 70 using adhesive bonds 72 or by any other design. Substrate 50 has an optically inactive surface 51 and an optically active surface 52. Reagents, such as labeled targets are injected into the cavity 71 through inlet port 73 by a pump 75 (FIG. 2) or by using a syringe, as described in U.S. Pat. No. 5,631,734, which is incorporated by reference. Within cavity 71, the reagents bind with one or more complementary probes located on surface 52 (located inside cavity 71 in the embodiment of FIG. 2). The reagents are circulated into the cavity via inlet port 73 by pump 75 and exit through outlet port 74 for re-circulation or disposal. A user can change hybridization conditions without removing substrate 50. Flow cell 70 may also include a temperature controller connected to a re-circulating bath device 76, as described in U.S. Pat. No. 5,631,734. Flow cell 70 may also include an agitation system and several valves, containers and cavities as described in U.S. Pat. Nos. 5,945,335 and 6,140,044, which are incorporated by reference.

Referring to FIG. 3, optically transparent substrate 50 has optically active surface 52 with a dense array of micro-optical elements 54. Micro-optical elements 54 may be formed by microlens cavities 56 or any other optical elements that provide "increased intensity" radiation or "evanescent" radiation. In the embodiment of FIG. 3, micro-optical elements 54 include microlens cavities 56 with a high index film (coating or layer) 58 deposited by sputtering or another vacuum deposition.

Microlens cavities 56 have a radius or a width (section or another relevant dimension) in the range of 100 nm to 1 μm; that is, a fraction or a small multiple of the wavelength of interest. The diameter and depth of the microlens cavities may define the thickness of the high index layer 58, which may even completely fill the cavities. High index layer 58 is made of titanium dioxide with an index of refraction of 2.4, gallium phosphate with an index of refraction 3.4, or other medium with suitable index of refraction. High index layer 58 is designed to have a thickness depending on its transmission coefficient so that a relatively low transmission coefficient will cause acceptable optical losses. Alternatively, micro-optical elements 54 are formed by parallel or semi-parallel groves, parallel or semi-parallel half cylinders, or other micro-structures.

Substrate 50 is made of a PMMA, Plexiglas® or a similar plastic with an index of refraction about 1.57. The microlens cavities could be created in the substrate by forced embossing at a proper temperature, or by casting against a suitably formed negative master (as used when creating CD and DVD discs). Alternatively, substrate 50 is be made by etching, which is preferably done for glass or quartz.

Micro-optical elements 54 may perform one or several functions. Micro-optical elements 54 may launch an evanescent surface wave 78 (FIG. 3) within biological material 68 (e.g., a spot of dehydrated or hydrated biological material). Micro-optical elements 54 may also serve as high NA optical element capable of gathering light emitted when the excitation radiation of the surface wave excites a fluorophore 69 located within or at the biological material. The micro-optical elements exhibit an efficient light gathering effect since they behave as a lenslets (or other optical elements) with a very high numerical aperture.

The shape of micro-optical elements 54 and the selection of the refraction index of substrate 50 permit the fluorescent emission from a fluorophore 69 to egress from the exposed surface of the support with a comparatively low divergence and preferably in a collimated manner, as shown by lines 67 in FIG. 3.

In the embodiment of FIG. 3, the emitted fluorescent radiation is collected by micro-optical elements 54 and transmitted back through the substrate. In this arrangement, a detector receives the transmitted fluorescent radiation via an objective lens (or optical system) located in a reflection geometry. Alternatively, the emitted fluorescent radiation is collected by a lens (or an optical system) located in a transmission geometry. In this embodiment, the detector receives fluorescent (or non-fluorescent) radiation that doesn't travel back through the substrate. In the transmission geometry, micro-optical elements 54 do not "intensify" the fluorescent radiation, but this radiation is not attenuated by the optically active substrate.

Referring to FIG. 1A, according to a first embodiment, scanning system 48 includes an oscillatory or rotary design for displacing an objective lens, for example, as described in PCT Application PCT/US99/06097 (published as WO 99/47964) or U.S. Provisional Application 60/286,578, both which are incorporated by reference. The rotary design caries a relatively simple and light objective lens, which is oscillated over the substrate area. The objective lens delivers an excitation light beam to an array of pixels of the scanned sample. The rotary design includes a periscopic structure that optically couples the scanning objective lens to the irradiation and detection light paths shown in FIG. 1.

In this embodiment, the rotary architecture offers both high speed scanning and a constant optical path length. The arc scanned by the objective lens covers the width of substrate 50 in polar coordinates. Substrate 50 is mounted on a translation stage for linear displacement. The data, acquired in polar coordinates for each slide position, is instantly converted to Cartesian coordinates by the instrument's computer so the image is then directly correlated with the microarray on substrate 50. The objective lens, carried on the rotary support structure may be an aspheric, one-element lens. Advantageously, the field of view is always on axis, which eliminates all the common sources of lateral or chromatic aberrations found in preobjective scanner microscopes.

According to another embodiment, beam scanning system 48 may include a rectilinear flying objective design, as described, in U.S. Pat. No. 5,459,325 to Hueton et al., which are incorporated by reference. The rectilinear flying objective design includes a lens mounted on a linear arm driven by a voice coil to perform a fast scan over sample substrate 50 in a first dimension. Substrate 50 is mounted on a translation stage that displaces sample in a second dimension, and may also move substrate 50 in a third dimension (i.e., z direction) for focusing.

The rectilinear flying objective design uses a reliable, low-cost, low-inertia, stable high-speed linear scanning system, which directly acquires the data in the Cartesian coordinate system. The optical data may be acquired in both directions of the lens scan, thus doubling the effective scanning speed. The scanning system includes an stable and rigid structure that enables high frequency scanning.

According to another embodiment, beam scanning system 48 may include a preobjective scanning design described in U.S. Pat. No. 5,981,956 to Stern or in U.S. Pat. No. 5,631,734 to Stern et al., both of which are incorporated by reference. The preobjective scanning design uses a scanning mirror that scans the excitation beam over a large field of view objective that includes several elements to provide, for example, a 10 mm field of view. This large field of view objective has a comparatively low NA of about 0.25. The examined substrate is translated linearly under the objective whiled the excitation beam is scanned over the objective by a scanning mirror. To scan an area larger than 10 mm wide, the optically active substrate can be translated sideways and scanned to capture a second swath. The two swaths are later stitched together by the instrument's computer. The major benefit of low numerical aperture (e.g., NA=0.25) is a large depth of field (e.g., 16 µm), which accommodates imperfections.

According to another embodiment, optical scanning system 10 may be replaced by an imaging system that uses a CCD array as described, for example, in U.S. Pat. No. 5,578,832, which is incorporated by reference.

Scanning and imaging systems 10 and 40 achieve a uniform performance (i.e., consistent data) over the entire surface of substrate 50. The intensity uniformity is about 95% and the spatial uniformity is about 98%. The system scan over a selected scan area (typically over a scan area of 20 mm×65 mm) and have a resolution of about 2.0 µm to 4.0 µm, wherein 10 µm is a sufficient resolution for a 10 µm spot size.

As known in the art and described, for example, in U.S. Pat. No. 5,910,940 an evanescent field arises at the boundary between a high refractive index medium and an adjacent lower index medium due to total internal reflection, as where the parent field in the higher index medium penetrates into the lower index medium (i.e., the refraction angle becomes imaginary). This evanescent field is a continuation of the internal standing wave that in turn is a result of constructive interference of incident and reflected illumination at the interface. (In the quantum mechanical view, this penetration of the total reflection barrier is called photon tunneling.) Immediately at the active layer (or low-index side of medium interface), the resultant intensity can be several times larger than the intensity of the incident radiation.

Evanescent field also arises when propagating illumination is diffracted by a grating having the grating period smaller than the wavelength, such that the diffracted orders are evanescent (i.e., the diffraction angle becomes imaginary). Again, the resultant intensity can be several times larger than the intensity of the incident radiation.

The amplitude of evanescent field decays exponentially with distance from the surface of the medium interface. The exponent of the decay depends on the ratio of denser to lower indices of refraction at the boundary surface. Thus, evanescent field decays over a distance of only less than a micron; thus this is "near-field." Near field includes both propagating and non-propagating radiation near, that is, within a wavelength of the interface surface. For interaction with biological medium 68, biological medium 68 has to be located close to the surface with the high-refractive index boundary (interface of the dielectric material), or close to the diffraction grating.

To increase the strength of the created evanescent radiation, higher refractive index medium is required. The index of refraction of available materials imposes a practical limit of about 2.4 in the visible spectrum, and about 3.5 in the near infra-red spectrum. Conversion by diffraction is limited only by the diffraction grating spatial period. The present embodiments can use a diffraction grating having the spatial period of less than 40 nanometers.

Different types of substrates have been used to excite evanescent radiation for use in microscopy, as described in U.S. Pat. Nos. 5,633,724; 5,437,840; or U.S. Pat. No. 5,351,127 to King or U.S. Pat. No. 5,341,215 to Seher, or European Patent Application 93304605.4 (EP 0575 132 A1) by King.

Alternatively, optically active substrate 52 includes an interference grating buried under a small layer of high index glass. This optically active substrate 52 is a modification of microscope slides described in U.S. Pat. Nos. 5,822,472 and 5,959,292 (which are incorporated by reference), and are available from Zeptosens AG (Witterswill Switzerland). The grating diffracts the incident light and/or light that has not been absorbed by the examined biological material (which is a very large fraction) and induces, at a suitable angle, an evanescent wave, which then interacts with the biological material. The intensity of the excited evanescent wave can be one order of magnitude greater than that of the original incident light beam. Since the grating reflects the beam at a different angle for each wavelength, each slide can operate beneficially at their designed wavelength.

Figure 4:
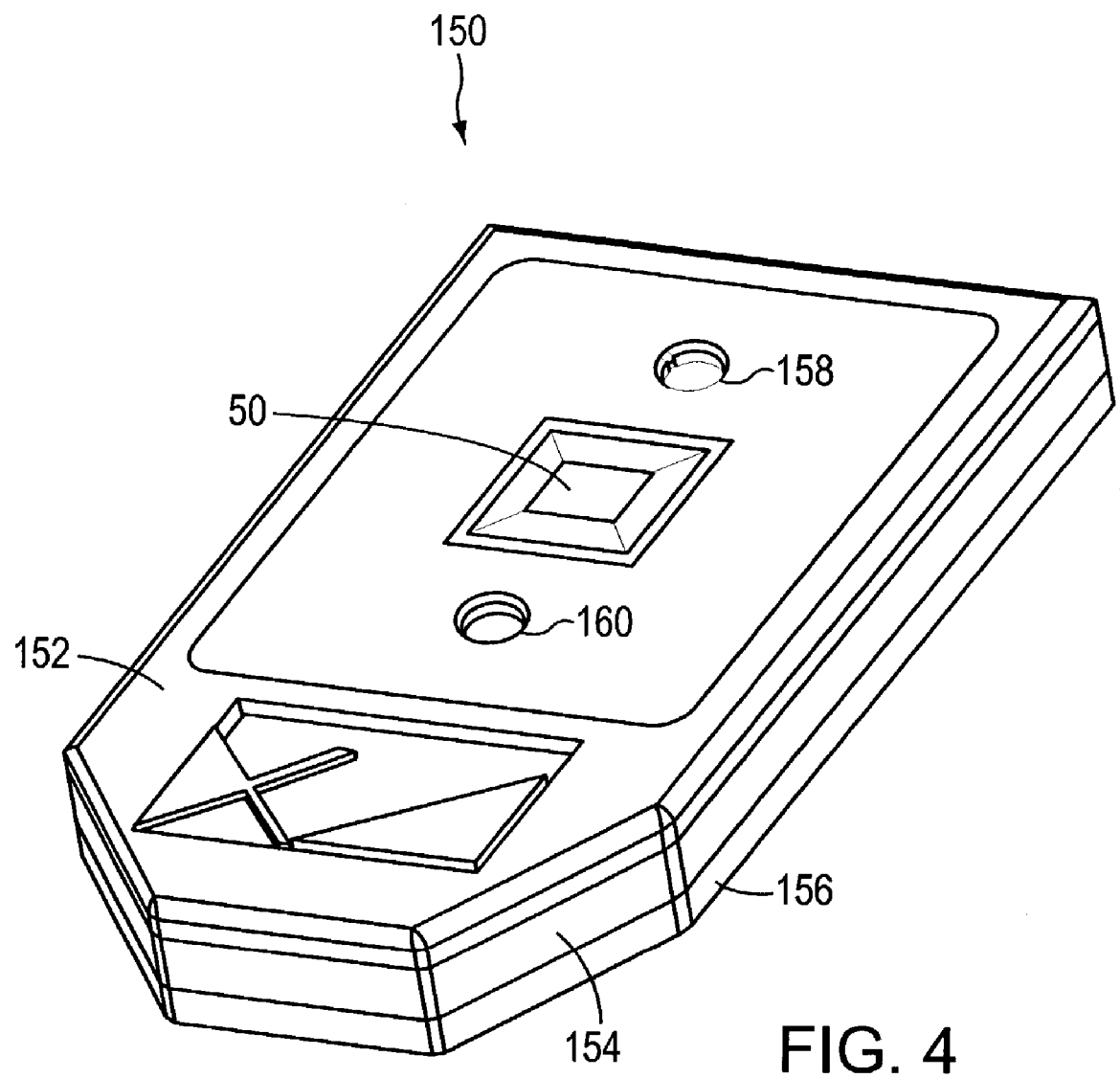
FIG. 4 shows an embodiment of a chip cartridge used for examination of biological material.

FIG. 4 show an embodiment of a cartridge 150 for packaging and handling substrate 50. Cartridge 150 includes a top casing 152, a middle casing 154 and a bottom casing 156 made of a plastic material and arranged to encase a hybridization cavity. Bottom casing 156 includes two fluid channels arranged in communication with two annular regions located in middle casing 154. Middle casing 14 includes a septum (or the like) located at the annular regions and arranged to seals fluids within two channels located in top casing 154 and in communication with the hybridization cavity, as described in detail in U.S. Pat. No. 5,945,334, which is incorporated by reference. Chip package 150 also includes alignment holes 158 and 160 and several support structures for mounting or positioning the chip package relative to a scanner.

The probe arrays may be fabricated according to various techniques disclosed in U.S. Pat. No. 5,143,854 to Pirrung et al., PCT Application WO 92/10092, or U.S. Pat. Nos. 5,384,261; 5,405,783; 5,412,087; 5,424,186; 5,445,934; or 5,744,308 all of which are incorporated by reference. As described above, micro-optical elements 54 provide high energy gathering in the proximity of the biological material 68 located on the probe arrays.

In general, a probe is a surface-immobilized molecule that is recognized by particular target and is sometimes referred to as a ligand. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides or nucleic acids, oligosaccharides, proteins, and monoclonal antibodies.

A target is a molecule that has an affinity for a given probe and is sometimes referred to as a receptor. Targets may be naturally-occurring or manmade molecules. Also, they can be employed in their unaltered state or as aggregates with other species. Targets may be attached, covalently or non-covalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides or nucleic acids, peptides, cofactors, lectins, sugars, polysaccharides, cells, cellular membranes, and organelles. Targets are sometimes referred to in the art as anti-probes or anti-ligands. As the term "targets" is used herein, no difference in meaning is intended. A "probe target pair" is formed when two macromolecules have combined through molecular recognition to form a complex.

Substrate 50 is preferably optically transparent, but it does not need to be optically transparent, for example, if used having optically active surface 52 facing incoming radiation beam 46. Substrate 50 may be fabricated of a wide range of material, either biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is preferably flat but may take on a variety of alternative surface configurations. For example, the substrate may contain raised or depressed regions on which a sample is located. The substrate and its surface preferably form a rigid support on which the sample can be formed. The substrate and its surface are also chosen to provide appropriate light-absorbing characteristics. For instance, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, or combinations thereof. Other materials with which the substrate can be composed of will be readily apparent to those skilled in the art upon review of this disclosure.

While the invention has been described with reference to the above embodiments, the present invention is by no means limited to the particular constructions described and/or shown in the drawings. The present invention also comprises any modifications or equivalents within the scope of the following claims.

The invention claimed is:

1. A device for optical examination of biological material using radiation of a selected wavelength, comprising an optically transparent substrate having a first surface and a second surface opposite to the first surface, the first surface comprising a dense array of micro-optical elements including a high index medium transparent at the wavelength and each having a dimension less than 100 µm, said dense array of micro-optical elements being arranged to provide increased intensity radiation near the micro-optical elements, the first surface being in close proximity to the examined biological material.

2. The device of claim 1 wherein the second surface is oriented for receiving the radiation emitted from a light source of an optical system.

3. The device of claim 2 wherein the second surface is oriented for providing radiation to a detector of an optical system after interaction of the increased intensity radiation with the biological material.

4. The device of claim 1 wherein each said micro-optical element has a dimension comparable to the wavelength of the radiation.

5. The device of claim 1 wherein the micro-optical elements are micro-lenses.

6. The device of claim 5 wherein the micro-lenses are formed by micro-cavities formed inside the substrate.

7. The device of claim 5 wherein the micro-lenses are formed by micro-cavities having parallel or semi parallel groves in the form of half cylinders or quarter cylinders.

8. The device of claim 6 wherein the micro-cavities are formed inside the substrate by spherical indentations one radius in depth.

9. The device of claim 1 wherein the micro-optical elements comprise a grating.

10. The device of claim 1 wherein the micro-optical elements are teeth-like structures.

11. The device of claim 1 wherein the optically transparent substrate has a thickness between the first and second surface of about 1 mm.

12. The device of claim 1 wherein the high index medium is deposited by one of the following: sputtering, evaporation, MOCVD.

13. The device of claim 1 wherein the micro-optical elements include high density micro-lenses having a high index of refraction.

14. The device of claim 13 wherein the high density micro-lenses include the high index of refraction made by deposition onto the first surface.

15. The device of claim 1 wherein the micro-optical elements are micro-lenses formed by micro-cavities inside the substrate, the micro-cavities having a radius in the range of 0.1 µm to 10 µm.

16. The device of claim 1 wherein the micro-optical elements are micro-lenses formed by micro-cavities inside the substrate, the micro-cavities having a radius less than 100 µm.

17. The device of claim 1 wherein the micro-optical elements are micro-lenses formed by micro-cavities inside the substrate and wherein a diameter and depth of the micro-cavities define the thickness of said high index medium deposited on the first surface.

18. The device of claim 17 wherein the high index medium is deposited by one of the following: sputtering, evaporation or MOCVD.

19. The device of claim 17 wherein the high index medium is made of titanium dioxide with an index of refraction of about 2.4.

20. The device of claim 17 wherein the high index medium is made of gallium phosphate with an index of refraction of about 3.4 or other medium with suitable index and transmission coefficient at the wavelength.

21. The device of claim 17 wherein the high index medium has a thickness of about 10 angstrom to 1000 angstrom depending on the material so that a relatively low coefficient of transmission of the material causes acceptable optical losses.

22. The device of claim 1 wherein the optically transparent substrate is made of one of the following: polycarbonate disc, Mylar based disc, PMMA disc, Plexiglas disc or similar plastic disc with an index of refraction about 1.57.

23. The device of claim 1 wherein the substrate is made of a material transparent to fluorescent light emitted from fluorophores associated with said examined biological material, said wavelength being selected to excite said fluorophores.

24. The device of claim 1 wherein said examined biological material is associated with a probe array supported by said high index medium.

25. The device of claim 24 wherein said examined biological material is associated with a fluorescent label capable of emitting fluorescent radiation after being irradiated by light of said selected wavelength.

26. The device of claim 24 wherein said probe array supported is deposited onto in contact with said high index medium.

27. The device of claim 26 wherein the second surface is oriented for receiving the radiation emitted from a light source of an optical system.

28. The device of claim 27 wherein the micro-optical elements comprise micro-lenses.

29. The device of claim 28 wherein the micro-lenses are formed by micro-cavities formed inside the substrate.

30. The device of claim 28 wherein the micro-lenses are formed by micro-cavities having parallel or semi parallel groves in the form of half cylinders or quarter cylinders.

31. The device of claim 24 wherein the micro-optical elements comprise a grating.

32. The device of claim 24 wherein the micro-optical elements comprise teeth-like structures.

33. The device of claim 24 wherein said probe array is created by a radiation directed synthesis.

34. The device of claim 24 wherein said probe array is created by a microfluidic delivery.

35. The device of claim 24 wherein said probe array includes fluorescently labeled biological polymers.

36. The device of claim 1 wherein said biological material is deposited in contact with said high index medium.

37. The device of claim 36 wherein the second surface is oriented for receiving the radiation emitted from a light source of an optical system.

38. The device of claim 37 wherein the micro-optical elements comprise micro-lenses.

39. The device of claim 38 wherein the micro-lenses are formed by micro-cavities formed inside the substrate.

40. The device of claim 38 wherein the micro-lenses are formed by micro-cavities having parallel or semi parallel groves in the form of half cylinders or quarter cylinders.

41. The device of claim 37 wherein the micro-optical elements comprise a grating.

42. The device of claim 37 wherein the micro-optical elements comprise teeth-like structures.

43. The device of claim 37 wherein said biological material includes fluorescently labeled biological polymers.

44. A device for optical examination of a probe array using radiation of an irradiation wavelength, said device comprising an optically transparent substrate having a first surface and a second surface opposite to the first surface, the first surface comprising a dense array of micro-optical elements being arranged to generate increased intensity radiation near the micro-optical elements, the first surface being arranged to provide support for the probe array, wherein each said micro-optical element has a dimension less than 100 µm and said micro-optical elements enable a surface wave.

45. The device of claim 44 wherein the second surface is oriented for receiving the radiation emitted from a light source of an optical system.

46. The device of claim 45 wherein the second surface is oriented for providing radiation to a detector of an optical system after interaction of the increased intensity radiation with elements of the probe array.

* * * * *